United States Patent [19]

Foster et al.

[11] 4,226,786

[45] Oct. 7, 1980

[54] PROCESS FOR DEHYDROGENATION OF STEROLS TO PRODUCE $\Delta^4$-3-KETOSTEROIDS (II)

[75] Inventors: Charles H. Foster; Donald R. Nelan, both of Kingsport, Tenn.

[73] Assignee: Eastman Kodak Company, Rochester, N.Y.

[21] Appl. No.: 81,957

[22] Filed: Oct. 4, 1979

[51] Int. Cl.$^3$ .............................................. C07J 9/00
[52] U.S. Cl. .................................................. 260/397.2
[58] Field of Search ........................ 260/397.25, 397.2

[56] References Cited

U.S. PATENT DOCUMENTS

| | | | |
|---|---|---|---|
| 4,072,697 | 2/1978 | Sekine et al. ..................... | 260/397.25 |
| 4,148,810 | 4/1979 | Struve .............................. | 260/397.25 |

Primary Examiner—Elbert L. Roberts
Attorney, Agent, or Firm—Clyde L. Tootle; Daniel B. Reece, III

[57] ABSTRACT

This invention relates to the dehydrogenation of a 3-$\beta$-hydroxy steroid or a mixture of soy sterols to form the corresponding mixture of $\Delta^4$-3-keto derivatives of phytosterols, the improvement which comprises dehydrogenation of the steroid or mixture of sterols using a supported nickel catalyst and carrying out the dehydrogenation in the presence of at least two chemically different hydrogen acceptors. One such process uses a supported nickel catalyst and a dialkyl ketone, such as methyl ethyl ketone, and an olefin, such as 1-hexene, as the two different hydrogen acceptors.

13 Claims, No Drawings

PROCESS FOR DEHYDROGENATION OF STEROLS TO PRODUCE $\Delta^4$-3-KETOSTEROIDS (II)

This invention relates to the dehydrogenation of a 3-$\beta$-hydroxy steroid or a mixture of soy sterols to form the corresponding $\Delta^4$-3-keto derivatives of phytosterols using a supported nickel catalyst and in the presence of two chemically different hydrogen acceptors.

The naturally occurring phytosterol components of vegetable oils such as soy oils are composed of mixtures of phytosterols which can be used in the preparation of certain pharmaceuticals such as progesterone which also can be used to prepare other steroids, such as cortisone and the like. However, an economical route to the preparation of progesterone from soy sterols involves first the oxidation of such sterols to the 4-en-3-one derivatives as the initial step. The 3$\beta$-OH of the sterol is oxidized to a ketone with rearrangement of the $\Delta^5$ double bond into conjugation with the ketone. Catalytic dehydrogenation is an economical method for this oxidation-rearrangement process. This catalytic dehydrogenation provides a process for the catalytic oxidation of $\Delta^5$-sterols to ketones with a simultaneous shift of the $\Delta^5$ double bond to the $\Delta^4$ position in conjugation with the carbonyl group. Raney nickel has also been used for this reaction, as disclosed in Chakravarti, Chackravarti, and Metra, *Nature*, 193, 1071 (1962) or in the presence of a hydrogen acceptor as disclosed in E. C. Kleiderer, and E. C. Kornfeld, *J. Org. Chem.*, 13, 455 (1948) and Kleiderer, Rice, Conquest and Williams, U.S. Dept. of Commerce, Office of the Publication Board, Report PB 981, 1945. If would therefore be an advance in the state of the art to provide an improved process for the catalytic dehydrogenation of soy sterols.

In accordance with the present invention 3-$\beta$-hydroxy steroid or a mixture of soy sterols can be dehydrogenated to the corresponding $\Delta^4$-3-ketosteroids using a supported nickel catalyst in the presence of two different hydrogen acceptors.

The supported nickel catalyst can be conventional supported active prereduced nickel supported catalysts such as nickel on Kieselguhr, silica or a silica/alumina or other suitable support which catalyst has been stabilized such as Girdler G-65S-RS (United Catalyst Co.). The dehydrogenation is carried out in the presence of at least two different hydrogen acceptors. One of the hydrogen acceptors is a dialkyl ketone and the other hydrogen acceptor is a 1-olefin. Useful dialkyl ketones are for example, methyl ethyl ketone, dimethyl ketone, diethyl ketone and the like. Useful 1-olefins are for example, 1-butene, 1-pentene, 1-hexene, 1-heptene, 1-octene and the like.

The 1-olefin is employed in an amount less than one equivalent, by weight, of the steroid or soy sterols. Greater amounts of 1-olefin tend to cause a decrease in the dehydrogenation reaction rate. Preferably, the amount of 1-olefin employed is about 20 percent by weight of the steroid or soy sterols.

The amount of dialkyl ketone employed is an amount at least the same as the 1-olefin and preferably about 5 to 10 times the amount. Since the dialkyl ketone is used as both a hydrogen acceptor and solvent for the reaction, an excess amount of the dialkyl ketone is generally used.

The dehydrogenation is preferably carried out at elevated temperatures such as about 150° C. to about 350° C., preferably 200° C.-300° C., most preferably 240°-260° C. At temperatures lower than 150° C., the dehydrogenation reaction is too slow and above 350° C. there is decomposition of the sterols. Since the dehydrogenation temperature is greater than the boiling point of some of the hydrogen acceptors, the reaction is preferably carried out under pressure in an autoclave or similar pressure vessel. The period of time used for the dehydrogenation depends on the temperature used. However, at temperatures of 200° C.-300° C. the reaction is substantially completed after about 8 hours.

The amount of catalyst employed varies with the amount of steroid or soy sterol used and the speed of reaction desired for the dehydrogenation reaction. Generally, an amount of catalyst used can be equal to about 20 to 100 percent, preferably 60 to 100 percent, based on the weight of the steroid or soy sterols to be used.

This invention can be further illustrated by the following examples, although it will be understood that these examples are included merely for purposes of illustration and are not intended to limit the scope of the invention unless otherwise specifically indicated.

EXAMPLE 1

Preparation of $\Delta^4$-3-derivatives of soy sterols was carried out using 20 g. of mixed soy sterols ($\sim$60% assay for total soy sterols) combined with 150 ml of methyl ethyl ketone and 13 ml of 1-hexene and 10 g. of Girdler G-65S-RS catalyst. After heating at 250° C. for 4 hrs. in an autoclave, the $\Delta^4$-3-keto derivatives of soy sterols were the only product obtained as determined by GLC and there was 75% conversion. The $\Delta^4$-3-keto derivatives of soy sterols are then reacted by ozonolysis to form the 4-stigmasten-3-one-derived aldehyde material, 3-ketodinor-4-cholen-22-aldehyde, which can be isolated from the other $\Delta^4$-3-keto derivatives of soy sterols by either chromatography or by treatment with sodium bisulfite and extraction with a suitable organic solvent such as toluene.

EXAMPLE 2

Example 1 was repeated except that the reaction was continued for 8 hours instead of 4 hours. An 85% conversion was obtained and the product was the desired $\Delta^4$-3-ketosteroid mixture (80 parts) and the saturated ketosteroid mixture (7 parts).

EXAMPLE 3

Cholesterol (20 g), methyl ethyl ketone (150 ml), and Girdler G65-S-RS catalyst (10.0 g) and 1-hexene (13 g) were heated and rocked at 250° C. for 4 hours. An analysis by gas chromatography indicated conversion to a mixture of 4-cholesten-3-one (78 parts), cholesterol (4 parts), coprostanone (8 parts), and cholestanone (6 parts). Similar results are obtained when sitosterol is used in place of cholesterol.

EXAMPLE 4

Example 1 was repeated except toluene or dioxane was substituted for methyl ethyl ketone. GLC analysis of the products showed only 17–27% conversion to the desired products ($\Delta^4$-3-ketosteroids).

EXAMPLE 5

Example 1 was repeated except without the addition of 1-hexene. GLC analysis of the product showed a mixture of $\Delta^4$-3-ketosteroids (76%), saturated 3-ketosteroids (18%) and unreacted sterols (6%). This Example shows the undesirable saturated by products formed in the reaction when the 1-olefin is deleted.

The process of the present invention provides an improved method for the dehydrogenation of steroids and soy sterols to provide $\Delta^4$-3-ketosteroids. These 4-en-3-ones derivatives can be used to provide materials useful for preparation of valuable steroids such as the cortical steroids.

The invention has been described in detail with particular reference to preferred embodiments thereof, but it will be understood that variations and modifications can be effected within the spirit and scope of the invention.

We claim:

1. A process which comprises dehydrogenating a 3-$\beta$-hydroxy steroid or a mixture of soy sterols to form the corresponding $\Delta^4$-3-keto derivatives, the improvement which comprises dehydrogenating said steroid or mixture of soy sterols using a supported nickel catalyst in the presence of a dialkyl ketone and a 1-olefin.

2. A process according to claim 1 wherein said 3-$\beta$-hydroxy steroid is stigmasterol.

3. A process according to claim 2 wherein said catalyst is Girdler G-65S-RS.

4. A process according to claim 3 wherein said dialkyl ketone is methylethyl ketone.

5. A process according to claim 4 wherein said olefin is 1-hexene.

6. A process according to claim 1 wherein said 3$\beta$-hydroxy steroid is cholesterol.

7. A process according to claim 6 wherein said catalyst is Girdler G-65S-RS.

8. A process according to claim 7 wherein said dialkyl ketone is methyl ethyl ketone.

9. A process according to claim 8 wherein said olefin is 1-hexene.

10. A process according to claim 1 wherein said 3-$\beta$-hydroxy steroid is sitosterol.

11. A process according to claim 10 wherein said catalyst is Girdler G-65S-RS.

12. A process according to claim 11 wherein said dialkyl ketone is methyl ethyl ketone.

13. A process according to claim 12 wherein said olefin is 1-hexene.

* * * * *